United States Patent
Tanaka

(10) Patent No.: US 10,213,535 B2
(45) Date of Patent: Feb. 26, 2019

(54) BREAST PUMP

(71) Applicant: Murata Manufacturing Co., Ltd., Kyoto (JP)

(72) Inventor: Nobuhira Tanaka, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 93 days.

(21) Appl. No.: 15/297,308

(22) Filed: Oct. 19, 2016

(65) Prior Publication Data

US 2017/0035951 A1    Feb. 9, 2017

Related U.S. Application Data

(63) Continuation of application No. PCT/JP2015/068747, filed on Jun. 30, 2015.

(30) Foreign Application Priority Data

Jul. 11, 2014    (JP) .................................. 2014-143123

(51) Int. Cl.
*A61M 1/06* (2006.01)

(52) U.S. Cl.
CPC .............. *A61M 1/064* (2014.02); *A61M 1/06* (2013.01); *A61M 2205/3331* (2013.01)

(58) Field of Classification Search
CPC .................... A61M 1/06; A61M 1/064; A61M 2205/3331; A61M 1/0066; A61M 2205/0294
See application file for complete search history.

(56) References Cited

U.S. PATENT DOCUMENTS

| 6,547,756 B1 | 4/2003 | Greter et al. |
|---|---|---|
| 2005/0234400 A1 | 10/2005 | Onuki et al. |
| 2008/0177224 A1 | 7/2008 | Kelly et al. |
| 2011/0004154 A1 | 1/2011 | Van Schijndel et al. |
| 2012/0116298 A1 | 5/2012 | Van Schijndel et al. |
| 2012/0277636 A1 | 11/2012 | Blondheim et al. |
| 2013/0064683 A1* | 3/2013 | Oshima .................. F04B 23/04 417/44.1 |
| 2013/0178752 A1 | 7/2013 | Kodama et al. |

FOREIGN PATENT DOCUMENTS

| EP | 1468705 A2 | 10/2004 |
|---|---|---|
| JP | 2003-518412 A | 6/2003 |
| JP | 2005-279043 A | 10/2005 |
| JP | 2010-115517 A | 5/2010 |
| JP | 2011-507577 A | 3/2011 |
| JP | 2012-533390 A | 12/2012 |
| WO | 2012/141113 A1 | 10/2012 |

OTHER PUBLICATIONS

Written Opinion of WO2016/006494 dated Sep. 15, 2015.
International search report of WO2016/006494 dated Sep. 15, 2015.

* cited by examiner

*Primary Examiner* — Rebecca E Eisenberg
(74) *Attorney, Agent, or Firm* — Pearne & Gordon LLP

(57) ABSTRACT

A breast pump (10) includes a breast pump cup (11) that is mounted on a breast, a suction pump (21) that absorbs fluid from the breast side of the breast pump cup (11), a detector (32) that detects temporal change in a sucked state of the breast by the breast pump cup (11), and an indicator (39) and a pattern adjusting unit (33) that perform processing based on the temporal change in the sucked state, which has been detected by the detector (32).

10 Claims, 9 Drawing Sheets

THICKNESS DIRECTION

LENGTHWISE DIRECTION

WIDTH DIRECTION

BREAST PUMP

This application is a continuation of International Application No. PCT/JP2015/068747 filed on Jun. 30, 2015 which claims priority from Japanese Patent Application No. 2014-143123 filed on Jul. 11, 2004. The contents of these applications are incorporated herein by reference in their entireties.

FIELD OF THE DISCLOSURE

The present disclosure relates to a breast pump that is used for absorbing breast milk or the like.

DESCRIPTION OF THE RELATED ART

In recent years, an electric suction device (breast pump) capable of expressing breast milk easily has been spread. Normally, the breast pump is configured to include a breast pump cup that is mounted on a breast, a suction pump that absorbs fluid from the breast side (inner side) of the breast pump cup, and a container that stores therein breast milk. The breast pump can provide a massage effect on the breast so as to improve breast milk expression efficiency and reduce pain involved in breast milk expression by setting a pattern (hereinafter, referred to as a suction pattern) of temporal change in suction pressure appropriately, for example. There are a breast pump in which a plurality of settings of the suction pattern are prepared and a user can be made to select the setting of the suction pattern and a breast pump in which setting of the suction pattern can be rewritten (for example, see Patent Document 1).

Patent Document 1: Japanese Unexamined Patent Application Publication No. 2010-115517

BRIEF SUMMARY OF THE DISCLOSURE

With the above-described breast pump, setting of a suction pattern that is expected to be optimum is written at the manufacturing stage or before usage. However, individual constitutions and breast swelling degrees are extremely diverse and the set suction pattern is not necessarily realized as it is practically. Furthermore, when a user selects setting of the suction pattern that is expected to be optimum based on his(her) own determination, it is not easy for the user to determine the setting of the suction pattern optimum for himself(herself).

When a sensor detecting hardness of skin of a breast surface can be mounted on a breast pump cup additionally, a breast pump can perform processing of automatically setting an optimum suction pattern in accordance with the hardness of the skin of the breast surface. However, the breast pump cup is formed with an elastic material normally and it is not realistic to additionally mount the above-described sensor on the breast pump cup because it causes the configuration of the breast pump to be complicated and increases time and effort for an operation of preparing breast milk expression.

An object of the present disclosure is to provide a breast pump capable of performing processing in accordance with hardness of skin of a breast surface without directly detecting the hardness of the skin of the breast surface.

A breast pump according to an aspect of the present disclosure includes a suction unit, a suction pump, a detecting unit, and a controller. The suction unit is mounted on a breast. The suction pump absorbs fluid from the breast side of the suction unit. The detecting unit detects temporal change in a sucked state of the breast by the suction unit. The controller performs processing based on the temporal change in the sucked state, which has been detected by the detecting unit.

With this configuration, the temporal change in the sucked state of the breast by the suction unit is in accordance with hardness of skin of a breast surface on which the suction unit is mounted. Therefore, the processing based on the temporal change in the sucked state of the breast by the suction unit enables processing based on the hardness of the skin of the breast surface to be performed.

Furthermore, it is preferable that the detecting unit detect the sucked state of the breast by the suction unit based on suction pressure of the suction pump. With this configuration, the suction unit and a connection configuration thereof can be simplified without necessity for additionally providing a member serving as the detecting unit on the suction unit.

Furthermore, it is preferable that the suction pump include a piezoelectric element operating by application of driving voltage. In this configuration, frequency of the driving voltage that is applied to the piezoelectric element can be made to deviate from frequency of audible sound, thereby reducing operation sound in comparison with a power source such as a motor.

Moreover, it is preferable that the detecting unit detect a state of impedance of the piezoelectric element and detect suction pressure of the suction pump based on the detected state of the impedance of the piezoelectric element. In particular, it is preferable that the breast pump further include a storage unit which previously stores a correspondence relation between the state of the impedance of the piezoelectric element and the suction pressure of the suction pump, and the detecting unit detect the suction pressure of the suction pump by referring to the storage unit.

The state of the impedance of the piezoelectric element changes in accordance with the suction pressure of the suction pump. Accordingly, the sucked state of the breast by the suction unit can be detected based on the state of the impedance of the piezoelectric element. With this configuration, the sucked state of the breast by the suction unit can be detected without separately adding a member such as a pressure sensor.

Furthermore, it is preferable that the detecting unit detect amplitude of electric current flowing through the piezoelectric element as the state of the impedance of the piezoelectric element. The magnitude of the impedance of the piezoelectric element changes in accordance with the suction pressure of the suction pump. The magnitude of the impedance of the piezoelectric element can be calculated as an amplitude ratio between the current flowing through the piezoelectric element and driving voltage of the piezoelectric element. Accordingly, when the driving voltage of the piezoelectric element is known, the sucked state of the breast by the suction unit can be detected based on the amplitude of the current flowing through the piezoelectric element. The detecting unit can be realized easily because the amplitude of the current can be detected by a small-sized simple circuit.

Moreover, it is preferable that the detecting unit detect phase difference between current flowing through the piezoelectric element and driving voltage of the piezoelectric element as the state of the impedance of the piezoelectric element. The phase difference between the current flowing through the piezoelectric element and the driving voltage of the piezoelectric element changes in accordance with the suction pressure of the suction pump. Accordingly, the sucked state of the breast by the suction unit can be detected based on the phase difference between the current flowing through the piezoelectric element and the driving voltage of the piezoelectric element. By detecting the sucked state of the breast by the suction unit based on the phase difference, the sucked state of the breast by the suction unit can be grasped with high accuracy even under a condition in which the driving voltage and the temperature fluctuate.

Furthermore, it is preferable that the detecting unit detect resonant frequency of the piezoelectric element as the state of the impedance of the piezoelectric element, and the controller drive the piezoelectric element at the resonant frequency. The resonant frequency of the piezoelectric element changes in accordance with the suction pressure of the suction pump. Accordingly, the sucked state of the breast by the suction unit can be detected based on the resonant frequency of the piezoelectric element. In addition, vibration of the piezoelectric element can be maximized by adjusting the driving frequency of the suction pump to the resonant frequency of the piezoelectric element, thereby suppressing power necessary for obtaining desired suction pressure.

It is preferable that the breast pump further include a notification unit which makes notification of the state detected by the detecting unit. With this configuration, the notification unit enables a user to be notified of the hardness of the skin of the breast surface, so that the user can grasp abnormality and the like of the breast. As the notification unit, a liquid crystal display unit, a display lamp, a wireless communication unit, or the like can be used.

According to the present disclosure, in a breast pump, processing in accordance with hardness of skin of a breast surface can be performed without directly detecting the hardness of the skin of the breast surface.

Figure 3A:
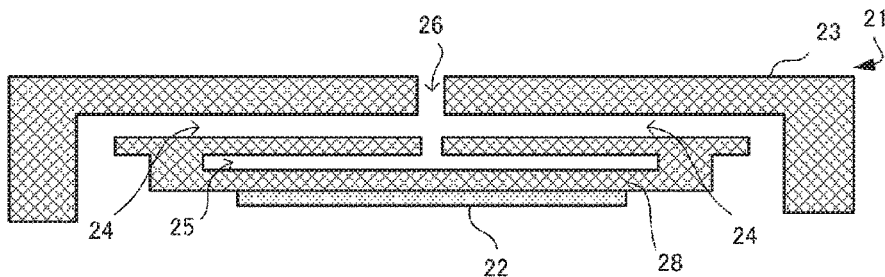
Figure 3B:
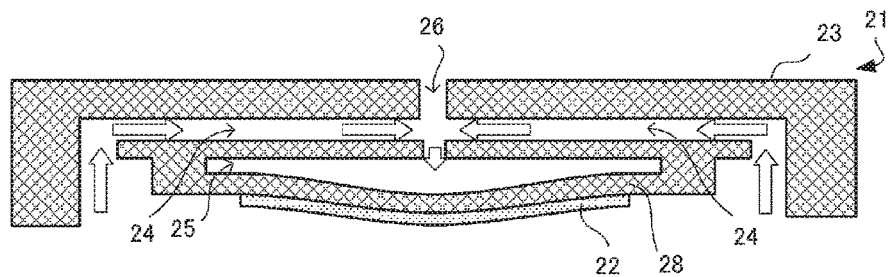
Figure 3C:
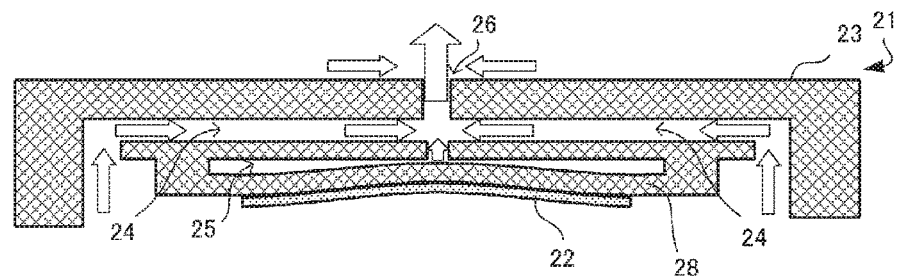

Each of FIGS. 3A, 3B and 3C is a schematic view illustrating a vibration manner of the suction pump in the first embodiment.

Figure 4:
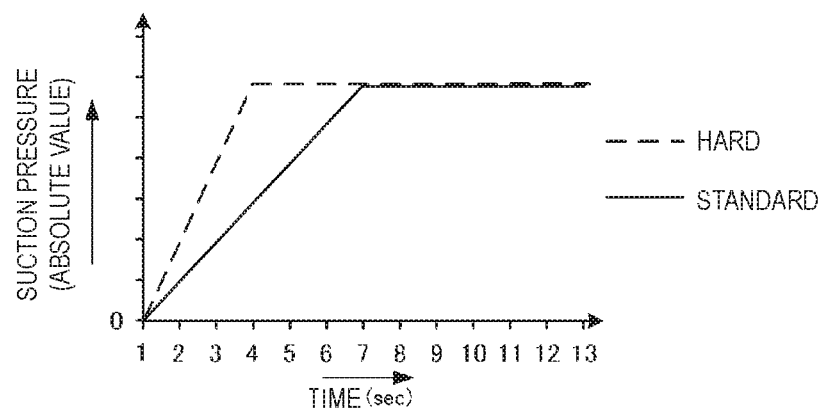

FIG. 4 is a graph illustrating temporal change in a sucked state of a breast by a breast pump cup in the first embodiment.

Figure 5:
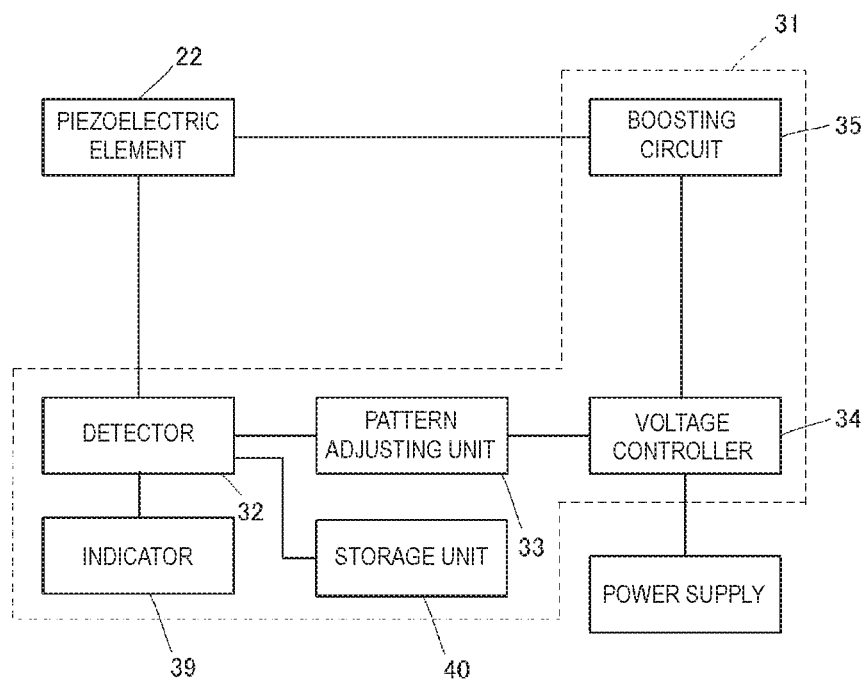

FIG. 5 is a block diagram illustrating a driving controller in the first embodiment.

Figure 6A:
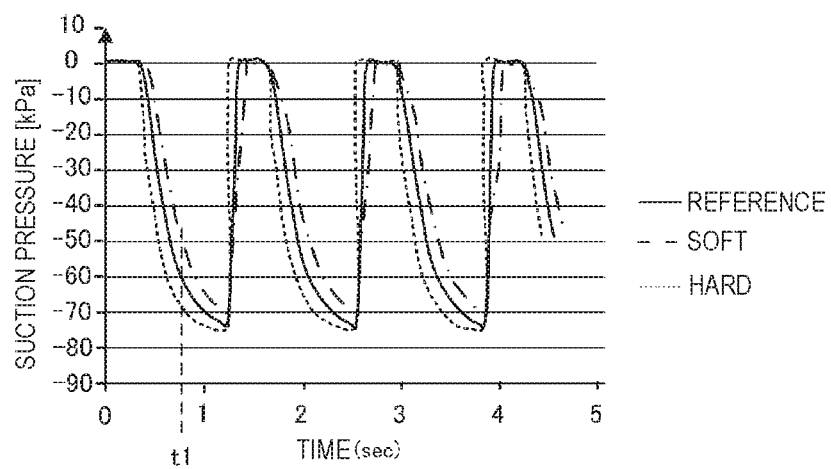
Figure 6B:
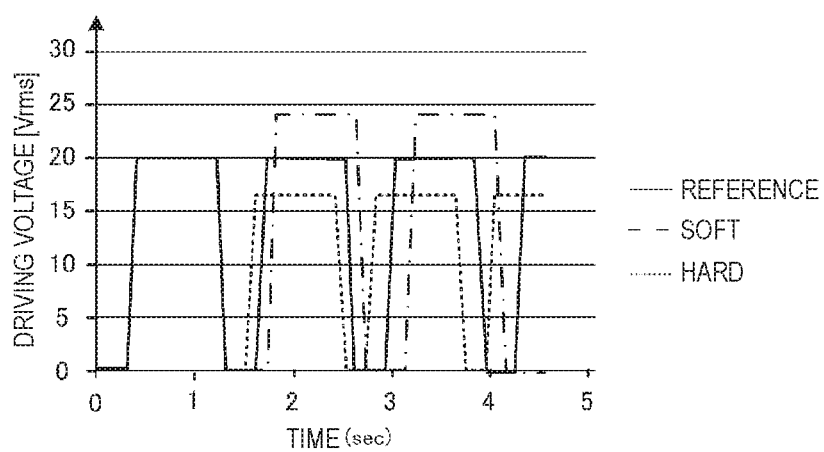
Figure 6C:
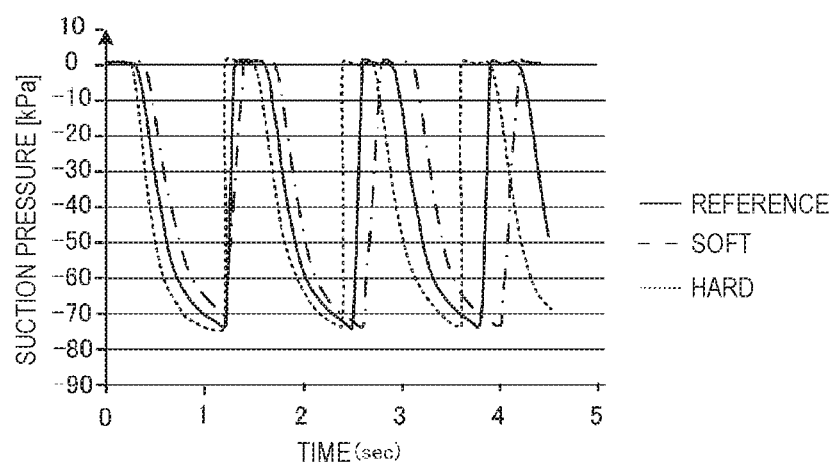

Each of FIGS. 6A, 6B and 6C is a graph illustrating an amplitude pattern of driving voltage that is applied to a piezoelectric element in the first embodiment.

Figure 7:
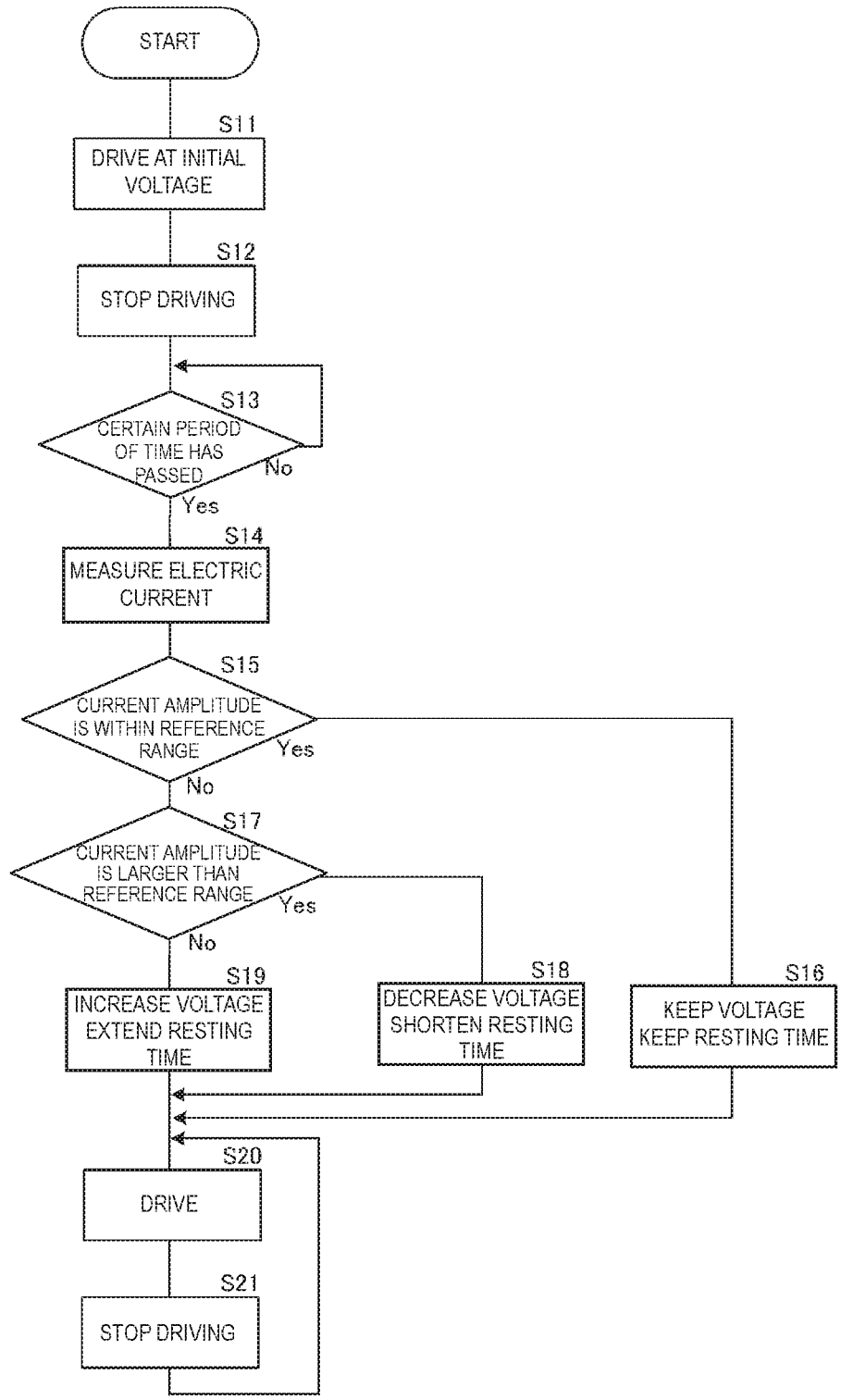

FIG. 7 is a flowchart illustrating operations of the driving controller in the first embodiment.

Figure 8:
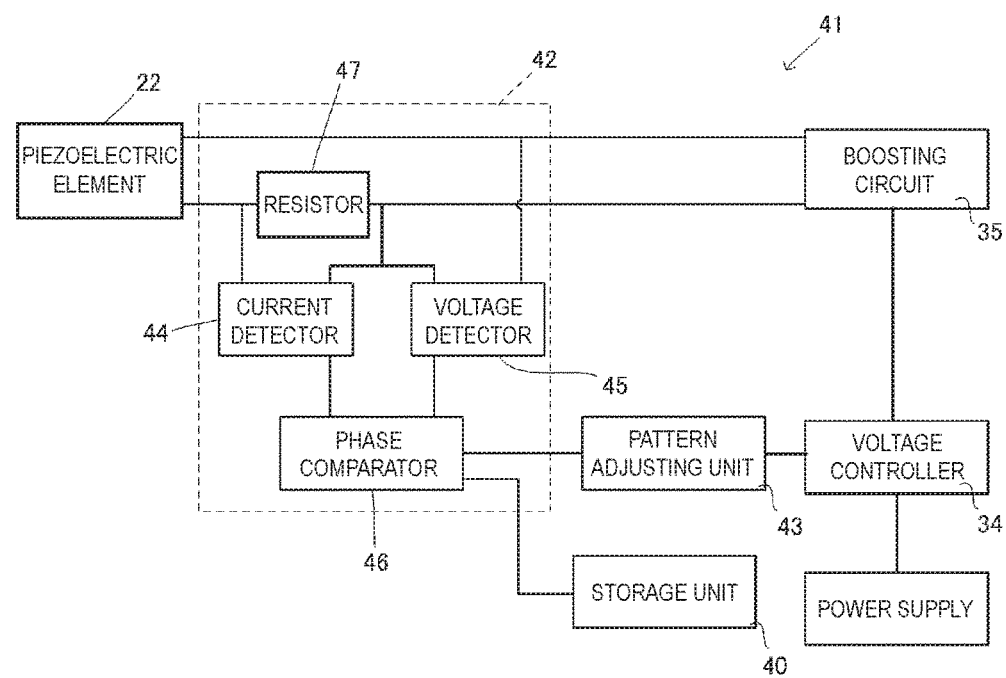

FIG. 8 is a block diagram illustrating a driving controller according to a second embodiment.

Figure 9:
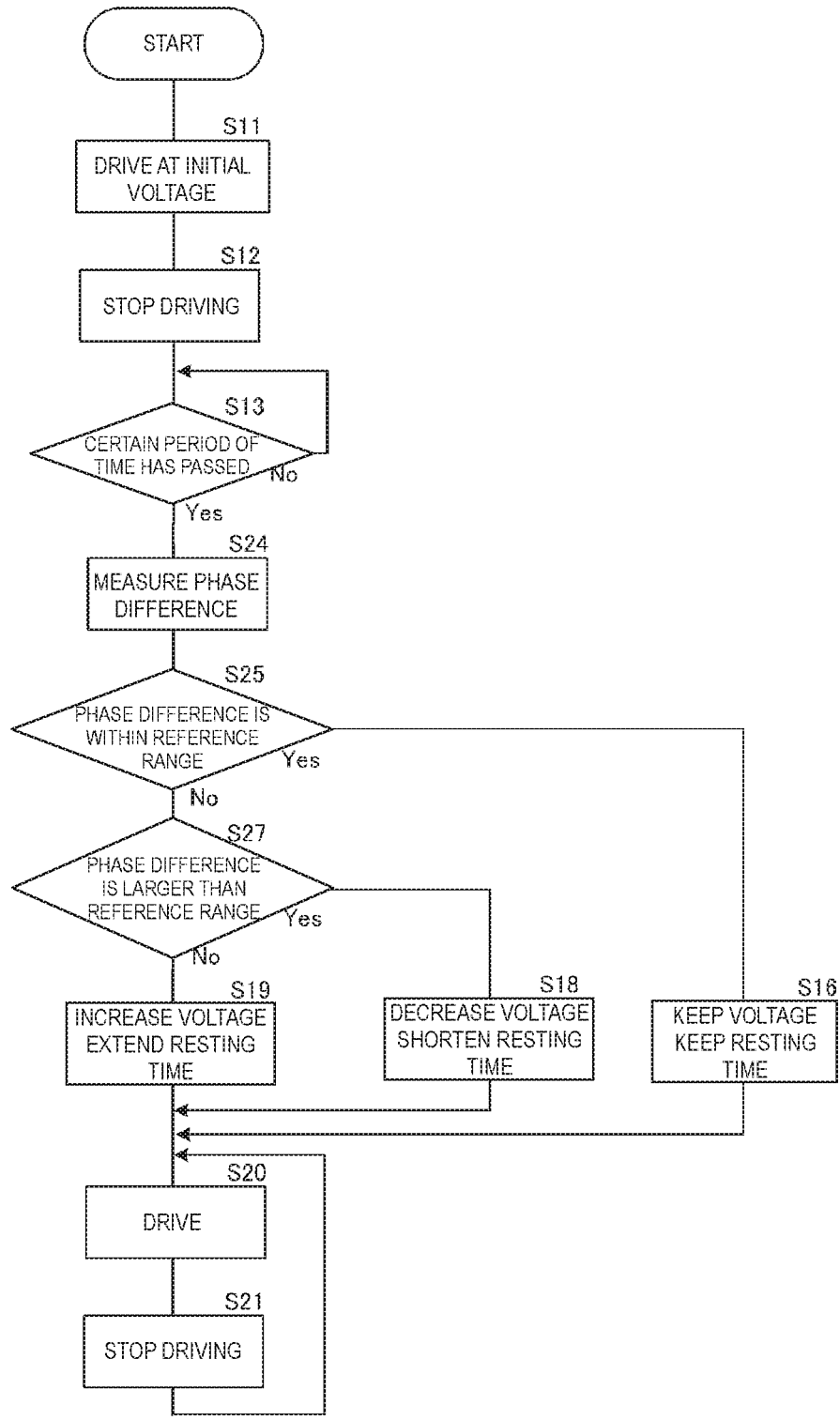

FIG. 9 is a flowchart illustrating operations of the driving controller in the second embodiment.

Figure 10:
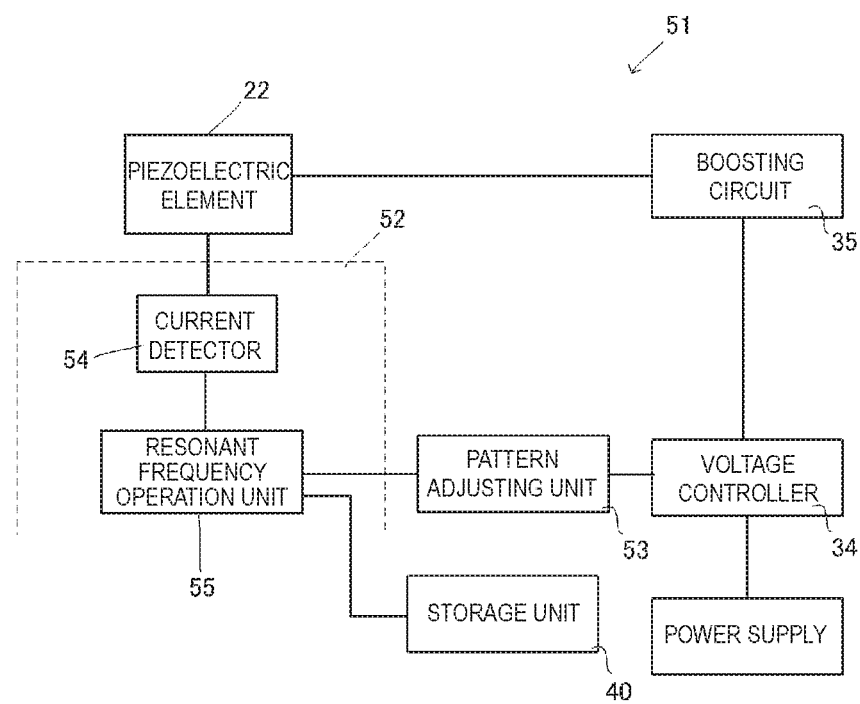

FIG. 10 is a block diagram illustrating a driving controller according to a third embodiment.

Figure 11:
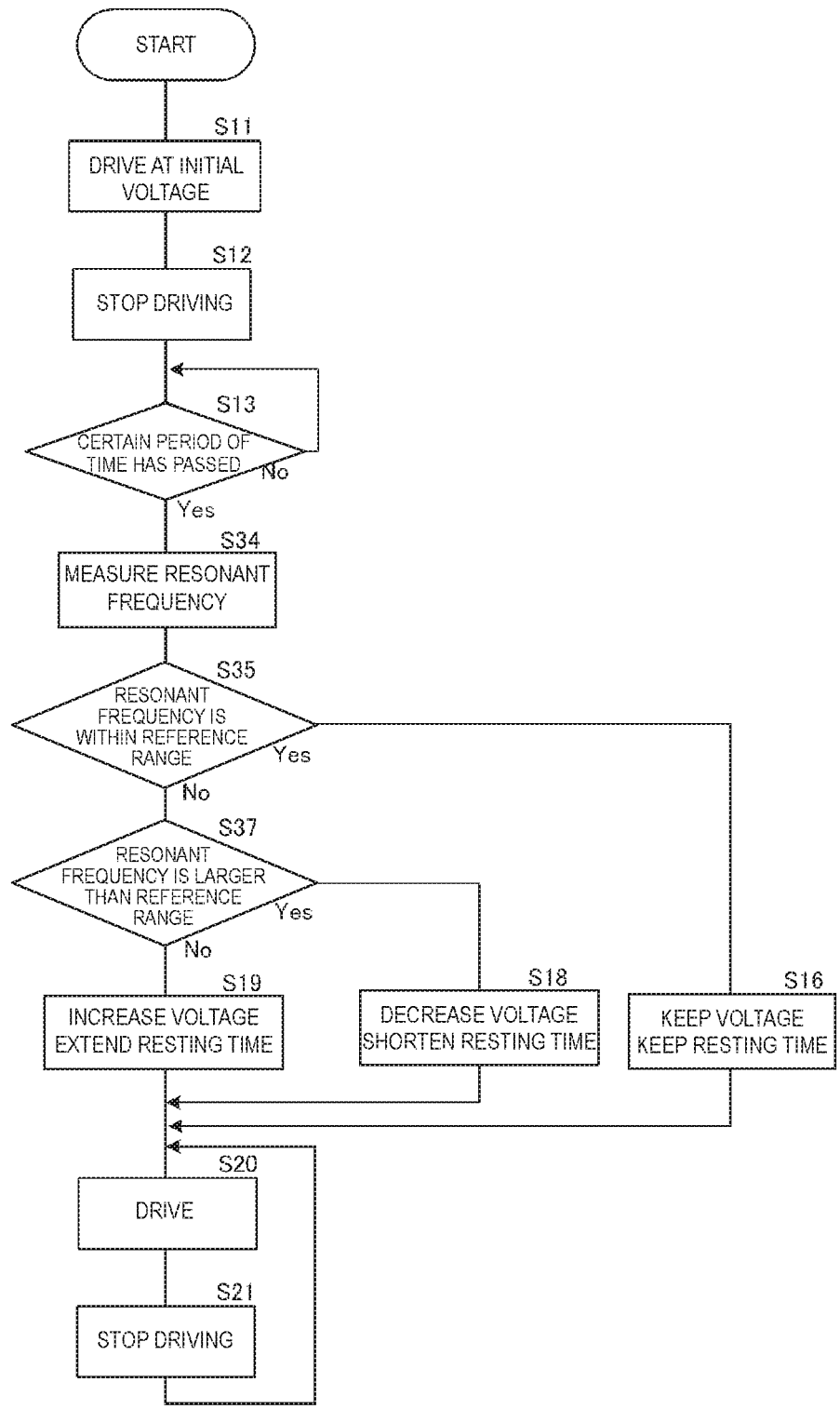

FIG. 11 is a flowchart illustrating operations of the driving controller in the third embodiment.

DETAILED DESCRIPTION OF THE DISCLOSURE

<<First Embodiment>>

Hereinafter, a breast pump 10 according to a first embodiment of the present disclosure will be described.

Figure 1:
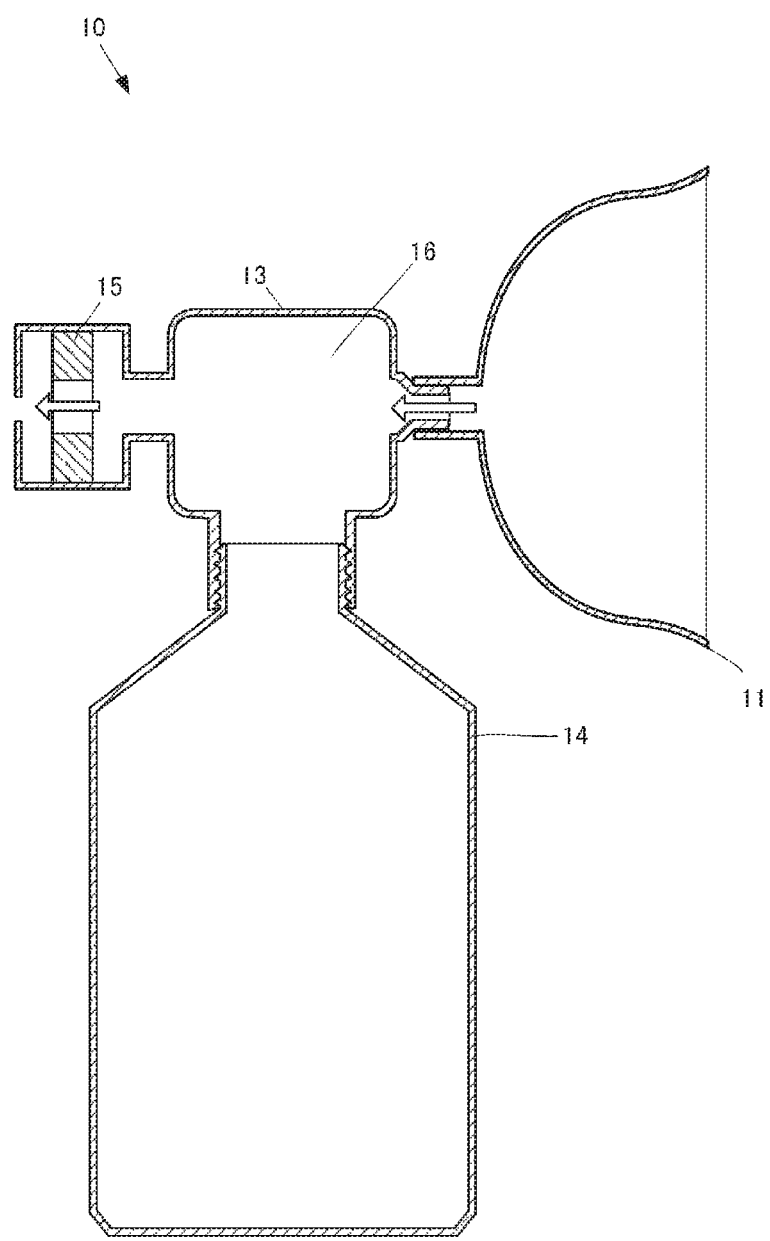
FIG. 1 is a schematic cross-sectional view illustrating a breast pump according to a first embodiment.

FIG. 1 is a schematic cross-sectional view illustrating the breast pump 10. The breast pump 10 includes a breast pump cup 11, a separator 13, a storage container 14, and a piezoelectric driving unit 15. The breast pump cup 11 corresponds to a suction unit according to the present disclosure and is formed into a vessel shape with a recessed surface along a breast surface. The breast pump cup 11 has a suction port at the center of the recessed surface. The separator 13 is formed into a container shape opened to the lower side. The storage container 14 is formed into a container shape opened to the upper side and is provided under the separator 13. Although not illustrated in FIG. 1, the breast pump 10 includes an indicator 39 (see FIG. 5) displaying a sucked state of a breast by the breast pump cup 11 and a valve for releasing internal pressure (suction pressure) of a flow path 16. Furthermore, the piezoelectric driving unit 15 includes a suction pump 21 (see FIG. 2) and a driving controller 31 (see FIG. 5).

The breast pump cup 11, the separator 13, and the piezoelectric driving unit 15 are connected in a state of being aligned in this order from the front side to the rear side of the breast pump 10. The flow path 16 communicating from the front end of the breast pump cup 11 to the rear end of the piezoelectric driving unit 15 is provided in the breast pump cup 11, the separator 13, the storage container 14, and the piezoelectric driving unit 15.

When the piezoelectric driving unit 15 is driven, fluid flow toward the rear end of the piezoelectric driving unit 15 from the recessed surface side (breast side) of the breast pump cup 11 is generated in the flow path 16. The breast pump cup 11 sucks the skin of the breast surface and absorbs breast milk from the breast. The separator 13 absorbs the breast milk from the breast pump cup 11 and causes the absorbed breast milk to drop downward. The storage container 14 stores therein the breast milk that drops from the separator 13.

Figure 2:
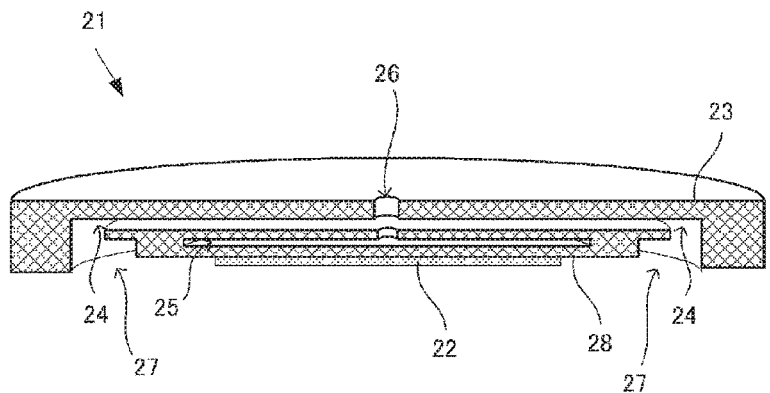
FIG. 2 is a cross-sectional view illustrating a suction pump in the first embodiment.

FIG. 2 is a cross-sectional view illustrating the suction pump 21. The suction pump 21 includes a piezoelectric element 22 and a structural body 23. The structural body 23 has a schematically disk-like outer shape that is thin in the thickness direction. A discharge port 26 is opened in the vicinity of the center of a top surface of the structural body 23. A suction port 27 is opened in the vicinity of an edge of the bottom surface of the structural body 23. The suction pump 21 is arranged such that the suction port 27 side is directed to the separator 13 side.

A flow path 24 and a pump chamber 25 are provided in the structural body 23. The flow path 24 communicates with the discharge port 26 in the top surface of the structural body 23, extends to the outer circumference side from the vicinity of the center in the structural body 23, and communicates with the suction port 27 in the bottom surface of the structural body 23. The pump chamber 25 is a thin cylindrical space provided at the bottom surface side of a communication portion between the discharge port 26 and the flow path 24 and is opened to the communication portion between the discharge port 26 and the flow path 24.

The inner bottom surface of the pump chamber 25 in the structural body 23 is configured as a diaphragm (vibration plate) 28 capable of vibrating in a bending manner. The diaphragm 28 has a disk-like shape and the top surface thereof faces the pump chamber 25. The top surface of the diaphragm 28 opposes the discharge port 26 with the pump chamber 25 interposed therebetween. The piezoelectric element 22 has a disk-like shape that is thin in the thickness direction and is bonded to the bottom surface of the diaphragm 28. The piezoelectric element 22 has piezoelectricity which makes it to extend and contract in the in-plane direction of a main surface thereof by application of alternating-current driving voltage.

Each of FIGS. 3A, 3B and 3C is a schematic view illustrating a vibration manner of the suction pump 21. The piezoelectric element 22 and the diaphragm 28 are bonded to each other to configure a unimorph structure, and are displaced in the thickness direction by driving of the piezoelectric element 22. To be specific, when the piezoelectric element 22 extends from a still state as illustrated in FIG. 3A, as illustrated in FIG. 3B, the diaphragm 28 is bent in a projecting form to the piezoelectric element 22 side (bottom surface side), so that a volume of the pump chamber 25 is increased. Therefore, negative pressure is generated in the pump chamber 25 and is transmitted to the flow path 24 communicating with the pump chamber 25. With this, the fluid in the flow path 24 is absorbed into the pump chamber 25.

When the piezoelectric element 22 contracts from the still state as illustrated in FIG. 3A, as illustrated in FIG. 3C, the diaphragm 28 is bent in a projecting form to the pump chamber 25 side (top surface side), so that the volume of the pump chamber 25 is decreased. With this, the fluid in the pump chamber 25 is discharged to the outside from the discharge port 26 and the fluid in the flow path 24 is discharged from the discharge port 26 by being drawn into the flow of the fluid because the pump chamber 25 and the discharge port 26 are opposed to each other with the flow path 24 interposed therebetween.

With the bending vibration of the piezoelectric element 22 and the diaphragm 28, in the suction pump 21, volume fluctuation and pressure fluctuation are periodically repeated in the pump chamber 25 and inertial force acts on gas flow. With this, gas flow with which the fluid in the flow path 24 is discharged from the discharge port 26 is generated constantly. In the suction pump 21, the diaphragm 28 is opposed to the discharge port 26 with the flow path 24 and the pump chamber 25 interposed therebetween. Therefore, fluid efficiency of the suction pump 21 is increased and high suction pressure and reduced power consumption can be realized at the same time.

Temporal change in a sucked state of the breast by the breast pump cup 11 in accordance with hardness of skin of the breast surface will be described.

FIG. 4 is a graph illustrating the temporal change in the sucked state of the breast by the breast pump cup 11 in a comparison manner between the case in which the breast pump cup 11 sucks the breast in a state of being not swollen with soft surface skin and the case in which the breast pump cup 11 sucks the breast in a state of being swollen with hard surface skin.

When the piezoelectric element 22 is driven at constant driving voltage such that maximum suction pressure of the breast pump is uniform, the suction pressure of the breast pump cup 11 that sucks the breast in the state of being not swollen and being soft is gradually increased from the driving start time and the degree of increase, that is, the temporal change in the suction pressure is relatively moderate because the breast in the state of being soft is easy to be sucked by the breast pump cup 11. Accordingly, when the breast in the state of being soft is sucked, a relatively long period of time is required to reach the maximum suction pressure from the driving start time. On the other hand, the suction pressure of the breast pump cup 11 that sucks the breast in the state of being swollen and being hard is gradually increased from the driving start time and the degree of increase, that is, the temporal change in the suction pressure is relatively steep because the breast in the state of being hard is difficult to be sucked by the breast pump cup 11. Accordingly, when the breast in the state of being hard is sucked, a relatively short period of time is required to reach the maximum suction pressure from the driving start time. Thus, the temporal change in the sucked state of the breast by the breast pump cup 11 differs depending on the swelling degree of the breast, that is, the hardness of the skin of the breast surface. Therefore, the hardness of the skin of the breast surface can be grasped based on the temporal change in the sucked state of the breast by the breast pump cup 11.

FIG. 5 is a block diagram illustrating an example of the configuration of the driving controller 31.

The driving controller 31 shown here has a function of detecting the sucked state of the breast by the breast pump cup 11 and controlling a pattern of the driving voltage and the driving time of the piezoelectric element 22. Furthermore, the driving controller 31 has a function of detecting the sucked state of the breast by the breast pump cup 11 based on impedance of the piezoelectric element 22.

The driving controller 31 includes a detector 32, a pattern adjusting unit 33, a storage unit 40, a voltage controller 34, a boosting circuit 35, and the indicator 39. The detector 32 configures a detecting unit according to the present disclosure.

The voltage controller 34 controls power supply voltage to supply it to the boosting circuit 35. The boosting circuit 35 boosts the power supply voltage to generate driving voltage and applies the driving voltage to the piezoelectric element 22. With this, the piezoelectric element 22 is driven to cause the breast pump 10 to absorb the breast milk.

The frequency of the driving voltage of the piezoelectric element 22 deviates from a frequency band of audible sound. Therefore, driving sound of the piezoelectric element 22 is softer than that of a motor and the like. Furthermore, the piezoelectric element 22 has property that impedance thereof is influenced by the pressure (suction pressure) of the fluid flowing through the flow path 24 illustrated in FIG. 2. Accordingly, when a correspondence relation between the suction pressure and the influence on the impedance of the piezoelectric element 22 is known, the suction pressure can be grasped based on the impedance of the piezoelectric element 22. Moreover, the suction pressure is influenced by the sucked state of the breast by the breast pump cup 11. Accordingly, when a correspondence relation between the sucked state of the breast by the breast pump cup 11 and the suction pressure is known, the sucked state of the breast by the breast pump cup 11 can be grasped based on the suction pressure.

The detector 32 detects a state of the impedance of the piezoelectric element 22. The storage unit 40 previously stores therein a correspondence relation between the state of the impedance of the piezoelectric element 22 and the suction pressure or the state of the breast pump cup 11 as a table or an operation expression. The detector 32 grasps the suction pressure and the state of the breast pump cup 11 based on the detected state of the impedance of the piezoelectric element 22 by referring to the storage unit 40. With this, the detector 32 can grasp temporal change in the suction pressure, temporal change in the sucked state of the breast by the breast pump cup 11, and the hardness of the skin of the breast surface based on temporal change in the state of the impedance of the piezoelectric element 22. The pattern adjusting unit 33 sets the voltage controller 34 so as to provide an optimum pattern of the driving voltage in accordance with the hardness of the skin of the breast surface based on a detection result of the detector 32 and the voltage controller 34 causes the boosting circuit 35 to output voltage. The voltage controller 34 transforms output voltage and controls a boosting ratio of the boosting circuit 35 so as to control the driving voltage that is output from the boosting circuit 35. The indicator 39 has a function of displaying information about the detection result of the detector 32 on a liquid crystal display unit, a display lamp, or the like, and a function of transmitting it to the outside with a communication line interposed therebetween. When the indicator 39 transmits the information to the outside with the communication line interposed therebetween, a user can grasp a state of the breast thereof and grasp the risk of generation of a disease or the like by causing an external device to display a breast swelling state in a time-series manner or determine and display an abnormal state of the breast swelling.

It should be noted that some of the functions of the pattern adjusting unit 33, the voltage controller 34, and the detector 32 can be configured by a single microcomputer, for example. For example, when a microcomputer performing PWM control is used, an I/O terminal of the microcomputer is connected to the detector 32 and a PWM output terminal of the microcomputer is directly connected to the boosting circuit 35. Furthermore, the microcomputer changes a duty ratio of PWM control output so as to control the driving voltage that is output from the boosting circuit 35.

The breast pump 10 can automatically set an optimum suction pattern in accordance with the hardness of the skin of the breast surface by configuring the driving controller 31 as described above. The detector 32 detects the hardness of the skin of the breast surface based on the impedance of the piezoelectric element 22. Therefore, a sensor detecting the hardness of the skin of the breast surface is not required to be provided on the breast pump cup 11, thereby preventing the configuration of the breast pump 10 from being complicated and preventing the time and effort for an operation of preparing breast milk expression from being increased.

FIG. 6A is a graph illustrating temporal change in the suction pressure when the pattern of the driving voltage is set such that driving voltage of predetermined amplitude is intermittently output. A solid line in FIG. 6A indicates temporal change in the suction pressure when the hardness of the skin of the breast surface is within a range of previously set reference hardness. A dashed line in FIG. 6A indicates temporal change in the suction pressure when the hardness of the skin of the breast surface is higher than the range of the previously set reference hardness. A dashed-dotted line in FIG. 6A indicates temporal change in the suction pressure when the hardness of the skin of the breast surface is lower than the range of the previously set reference hardness.

The case in which the hardness of the skin of the breast surface is within the previously set hardness range is assumed to be reference. Under this assumption, when the skin of the breast surface is hard, both of the falling of the suction pressure with application of the driving voltage to the piezoelectric element 22 and the rising of the suction pressure with the stoppage of the application of the driving voltage are steeper than the reference. On the other hand, when the skin of the breast surface is soft, both of the falling of the suction pressure with application of the driving voltage to the piezoelectric element 22 and the rising of the suction pressure with the stoppage of the application of the driving voltage are more moderate than the reference. When the falling of the suction pressure and the rising of the suction pressure are compared with each other, the temporal change in the suction pressure is more moderate at the time of the falling of the suction pressure.

Accordingly, the detector 32 detects the state of the impedance of the piezoelectric element 22 at a timing on the halfway of the falling of the suction pressure after a predetermined period of time has passed from the start of application of the driving voltage, which is as indicated by time t1 in FIG. 6A. Then, the detected state is compared with a corresponding state of the impedance at the reference suction pressure at the time t1, which has been previously grasped, thereby detecting the state of the breast.

FIG. 6B is a graph illustrating a pattern of the driving voltage that is set by the pattern adjusting unit 33, as an example. A solid line in FIG. 6B indicates an amplitude pattern of the driving voltage, which is set when the hardness of the skin of the breast surface is within the range of previously set reference hardness. A dashed line in FIG. 6B indicates an amplitude pattern of the driving voltage, which is set when the hardness of the skin of the breast surface is higher than the range of the previously set reference hardness. A dashed-dotted line in FIG. 6B indicates an amplitude pattern of the driving voltage, which is set when the hardness of the skin of the breast surface is lower than the range of the previously set reference hardness.

The pattern adjusting unit 33 sets a pattern of the driving voltage such that the driving voltage of predetermined amplitude is intermittently output at a constant period, for example. The detector 32 detects temporal change in the state of the impedance of the piezoelectric element 22 under a condition after a predetermined period of time has passed from application of the driving voltage in a first period. Then, the amplitude of the driving voltage in second and subsequent periods is changed based on the detection result thereof.

To be more specific, for example, when the hardness of the skin of the breast surface is within the range of the previously set reference hardness, the pattern adjusting unit 33 sets the pattern of the driving voltage in the second and subsequent periods so as not to change the driving voltage having the initial amplitude as it is. On the other hand, when the hardness of the skin of the breast surface is higher than the range of the previously set reference hardness, the pattern adjusting unit 33 sets the pattern of the driving voltage in the second and subsequent periods so as to change the driving voltage to have amplitude smaller than the initial amplitude and shorten resting time. Furthermore, when the hardness of the skin of the breast surface is lower than the range of the previously set reference hardness, the pattern adjusting unit 33 sets the pattern of the driving voltage in the second and subsequent periods so as to change the driving voltage to have amplitude larger than the initial amplitude and extend the resting time.

FIG. 6C is a graph illustrating temporal change in the suction pressure when the above-described change is set to the driving voltage. A solid line in FIG. 6C indicates temporal change in the suction pressure when the hardness of the skin of the breast surface is within the range of previously set reference hardness. A dashed line in FIG. 6C indicates temporal change in the suction pressure when the hardness of the skin of the breast surface is higher than the range of the previously set reference hardness. A dashed-dotted line in FIG. 6C indicates temporal change in the suction pressure when the hardness of the skin of the breast surface is lower than the range of the previously set reference hardness.

When the pattern of the driving voltage is changed as described above, the temporal change in the suction pressure in the second and subsequent periods differs from that in the case in which the pattern of the driving voltage is not changed as in FIG. 6A. To be specific, when the skin of the breast surface is hard, the application start timing of the driving voltage and the application stop timing of the driving voltage come earlier. On the other hand, when the skin of the breast surface is soft, the application start timing of the driving voltage and the application stop timing of the driving voltage come later. In addition, a waveform of the suction pressure in a falling period of the suction pressure, which is subsequent to the application start timing of the driving voltage, becomes uniform regardless of the hardness of the skin of the breast surface. Accordingly, even when the individual constitution and breast swelling degree are different, the set suction pattern that is expected to be optimum can be realized as it is. Therefore, breast milk expression efficiency can be enhanced regardless of the individual constitutions and the breast swelling degrees and pain felt by the user can be reduced.

It should be noted that a waveform of the suction pressure in a rising period of the suction pressure, which is subsequent to the application stop timing of the driving voltage, differs depending on the hardness of the skin of the breast surface. However, this difference gives almost no influence on the breast milk expression efficiency and the pain felt by the user.

Next, the function of detecting the sucked state of the breast by the breast pump cup 11 will be described more in detail.

The magnitude of the impedance of the piezoelectric element 22 is influenced by the sucked state of the breast by the breast pump cup 11. Furthermore, the magnitude of the impedance of the piezoelectric element 22 can be expressed as a ratio between the amplitude of the current flowing through the piezoelectric element 22 and the amplitude of the driving voltage that is applied to the piezoelectric element 22. Accordingly, when a correspondence relation among the sucked state of the breast by the breast pump cup 11, the amplitude value of the current flowing through the piezoelectric element 22, and the amplitude value of the driving voltage that is applied to the piezoelectric element 22 is known, the sucked state of the breast by the breast pump cup 11 can be grasped by detecting, by the detector 32, the amplitude value of the current and grasping output voltage of the boosting circuit 35.

FIG. 7 is a flowchart illustrating an example of operations of the driving controller 31 when change in the current flowing through the piezoelectric element 22 is detected for controlling the pattern of the driving voltage.

First, the driving controller 31 applies driving voltage set to have initial amplitude to the piezoelectric element 22 (S11). With this application, the piezoelectric element 22 is driven and the breast pump 10 starts an operation of absorbing breast milk using the breast pump cup 11. Then, the driving controller 31 stops application of the driving voltage to the piezoelectric element 22 (S12). Subsequently, the driving controller 31 waits for the predetermined time t1 on the halfway of the falling of the suction pressure, which is illustrated in FIG. 6A as described above, (Yes at S13) and measures the amplitude of the current flowing through the piezoelectric element 22 (S13→S14).

The time t1 is on the halfway of the falling of the driving voltage and the amplitude value of the driving voltage is approximately constant at the time t1 regardless of the hardness of the skin of the breast surface. Accordingly, the amplitude of the current flowing through the piezoelectric element 22 changes in accordance with the magnitude of the impedance of the piezoelectric element 22. Therefore, by previously grasping the range of the amplitude of the current flowing through the piezoelectric element 22 when the hardness of the skin of the breast surface is within the reference range and storing it in the storage unit or the like, whether the hardness of the skin of the breast surface is harder or softer than the reference can be grasped by comparing the amplitude of the current flowing through the piezoelectric element 22 with the reference range.

In consideration of this, the driving controller 31 compares the measured amplitude of the current with the previously registered reference range (S15 and S17). When the measured amplitude of the current is within the reference range (Yes at S15), the driving controller 31 keeps the driving voltage to the initial voltage and keeps the resting time to the predetermined setting (S16). When the measured amplitude of the current is larger than the reference range (Yes at S17), which means that the skin of the breast surface is harder than the reference, the driving controller 31 changes the driving voltage to driving voltage having amplitude decreased from that of the initial voltage and shortens the resting time from the predetermined setting (S18). When the measured amplitude of the current is smaller than the reference range (No at S17), which means that the skin of the breast surface is softer than the reference, the driving controller 31 changes the driving voltage to driving voltage having amplitude increased from that of the initial voltage and extends the resting time from the predetermined setting (S19).

Subsequently, the driving controller 31 sets the pattern of the driving voltage with the voltage amplitude and the length of the resting time as described above and applies the driving voltage to the piezoelectric element 22 (S20). Then, the driving controller 31 repeats application of the driving voltage to the piezoelectric element 22 (S20) and stoppage of the application of the driving voltage (S21).

As described above, when the pattern of the driving voltage to the piezoelectric element 22 is controlled by detecting the current flowing through the piezoelectric element 22, it is sufficient that the detector 32 has a function of detecting the current, thereby achieving an extremely simple circuit configuration reduced in size.

With the driving controller 31 described herein, the amplitude of the current flowing through the piezoelectric element 22 is larger than the reference range when the skin of the breast surface is harder than the reference whereas the amplitude of the current flowing through the piezoelectric element 22 is smaller than the reference range when the skin of the breast surface is softer than the reference. However, depending on the configuration of the suction pump 21 and the configuration of the driving controller 31, conversely, the amplitude of the current flowing through the piezoelectric element 22 is smaller than the reference range when the skin of the breast surface is harder than the reference whereas the amplitude of the current flowing through the piezoelectric element 22 is larger than the reference range when the skin of the breast surface is softer than the reference in some cases. Therefore, it is preferable that the amplitude of the driving voltage and the resting time in the above-described operation flow be appropriately set based on the actual correspondence relation between the hardness of the skin of the breast surface and the current flowing through the piezoelectric element 22.

<<Second Embodiment>>

Next, a breast pump according to a second embodiment of the present disclosure will be described.

The breast pump according to the second embodiment of the present disclosure is different from that in the first embodiment in the configuration of the detector detecting the sucked state of the breast by the breast pump cup 11 and the function of the pattern adjusting unit.

FIG. 8 is a block diagram illustrating a driving controller 41 included in the breast pump in the second embodiment.

The driving controller 41 that is described herein has a function of detecting the sucked state of the breast by the breast pump cup 11 based on phase difference between the current and the voltage in the piezoelectric element 22. The phase difference between the current flowing through the piezoelectric element 22 and the driving voltage changes in accordance with the suction pressure. Accordingly, when a correspondence relation between the sucked state of the breast by the breast pump cup 11 and the phase difference between the current and the voltage in the piezoelectric element 22 is known, the sucked state of the breast by the breast pump cup 11 can be grasped by detecting the phase of the current and the phase of the voltage.

The driving controller 41 includes a detector 42, a pattern adjusting unit 43, a storage unit 40, the voltage controller 34, and the boosting circuit 35. The detector 42 configures the detecting unit according to the present disclosure and includes a current detector 44, a voltage detector 45, a phase comparator 46, and a resistor 47. The current detector 44 measures voltage between both ends of the resistor 47 resistance value of which is known so as to measure the current flowing through the piezoelectric element 22. The resistor 47 is inserted in a voltage line connecting the piezoelectric element 22 and the boosting circuit 35. The voltage detector 45 measures driving voltage that is applied to the piezoelectric element 22. The phase comparator 46 outputs phase difference θ between the current measured by the current detector 44 and the voltage measured by the voltage detector 45. The pattern adjusting unit 43 sets the voltage controller 34 so as to provide an optimum pattern of the driving voltage in accordance with the sucked state of the breast by the breast pump cup 11 based on the phase difference θ output from the phase comparator 46 and the voltage controller 34 causes the boosting circuit 35 to output the voltage.

For example, a digital comparator having a circuit system, such as a phase frequency comparator that is used in a phase locked loop (PLL) or the like, can be used as the phase comparator 46. Moreover, some of the functions of the pattern adjusting unit 43, the voltage controller 34, and the detector 42 can be configured by a microcomputer, for example. For example, when a microcomputer performing PWM control is used, an I/O terminal of the microcomputer is connected to the detector 42 and a PWM output terminal of the microcomputer is directly connected to the boosting circuit 35. Furthermore, the microcomputer changes a duty ratio of PWM control output so as to control amplitude of the driving voltage that is output from the boosting circuit 35.

FIG. 9 is a flowchart illustrating an example of operations of the driving controller 41 when the phase difference between the above-described current flowing through the piezoelectric element 22 and the driving voltage is detected for controlling the pattern of the driving voltage of the piezoelectric element 22.

First, the driving controller 41 applies driving voltage set to have initial amplitude to the piezoelectric element 22 (S11). With this application, the piezoelectric element 22 is driven and the breast pump 10 starts an operation of absorbing breast milk using the breast pump cup 11. Then, the driving controller 41 stops application of the driving voltage to the piezoelectric element 22 (S12). Subsequently, the driving controller 41 waits for the predetermined time t1 on the halfway of the falling of the suction pressure, which is illustrated in FIG. 6A as described above, (Yes at S13) and measures the phase difference between the current flowing through the piezoelectric element 22 and the driving voltage (S13→S24).

Then, the driving controller 41 compares the measured phase difference with a previously registered reference range of the phase difference (S25 and S27). When the measured phase difference is within the reference range (Yes at S25), the driving controller 41 keeps the driving voltage to the initial voltage and keeps the resting time to the predetermined setting (S16). When the measured phase difference is larger than the reference range (Yes at S27), the driving controller 41 changes the driving voltage to driving voltage having amplitude increased from that of the initial voltage and shortens the resting time from the predetermined setting (S18). When the measured phase difference is smaller than the reference range (No at S27), the driving controller 41 changes the driving voltage to driving voltage having amplitude decreased from that of the initial voltage and extends the resting time from the predetermined setting (S19).

Subsequently, the driving controller 41 sets the pattern of the driving voltage with the voltage amplitude and the length of the resting time that are set as described above and applies the driving voltage to the piezoelectric element 22 (S20). Then, the driving controller 41 repeats the application of the driving voltage to the piezoelectric element 22 (S20) and the stoppage of the application of the driving voltage (S21).

As described above, when the pattern of the driving voltage to the piezoelectric element 22 is controlled by detecting the phase difference between the current flowing through the piezoelectric element 22 and the driving voltage, the sucked state of the breast by the breast pump cup 11 can be grasped with high accuracy even under a condition in which the driving voltage and the temperature fluctuate, thereby adjusting the suction pressure with high accuracy.

With the driving controller 41 described herein, the phase difference is larger than the reference range when the skin of the breast surface is harder than the reference whereas the phase difference is smaller than the reference range when the skin of the breast surface is softer than the reference. However, depending on the configuration of the suction pump 21 and the configuration of the driving controller 41, conversely, the phase difference is smaller than the reference range when the skin of the breast surface is harder than the reference whereas the phase difference is larger than the reference range when the skin of the breast surface is softer than the reference in some cases. Therefore, it is preferable that the amplitude of the driving voltage and the resting time in the above-described operation flow be appropriately set based on the actual correspondence relation between the hardness of the skin of the breast surface and the phase difference.

<<Third Embodiment>>

Next, a breast pump according to a third embodiment of the present disclosure will be described.

The breast pump according to the third embodiment of the present disclosure is different from those in the first embodiment and the second embodiment in the configuration of the detector detecting the sucked state of the breast by the breast pump cup 11 and the function of the pattern adjusting unit.

FIG. 10 is a block diagram illustrating a driving controller 51 included in the breast pump in the third embodiment.

The driving controller 51 that is described herein has a function of detecting the sucked state of the breast by the breast pump cup 11 based on resonant frequency of the piezoelectric element 22. The resonant frequency of the piezoelectric element 22 is frequency at which the magnitude of the impedance of the piezoelectric element 22 is minimum, that is, the amplitude of the current flowing through the piezoelectric element 22 is maximum. The resonant frequency of the piezoelectric element 22 can be calculated by changing the frequency of the driving voltage in a predetermined range, measuring the current flowing through the piezoelectric element 22 at each frequency, and selecting the frequency at which the amplitude of the measured current is maximum. Furthermore, the resonant frequency of the piezoelectric element 22 changes in accordance with the suction pressure. Accordingly, when a correspondence relation between the sucked state of the breast by the breast pump cup 11 and the resonant frequency of the piezoelectric element 22 is known, the sucked state of the breast by the breast pump cup 11 can be grasped by detecting the resonant frequency.

The driving controller 51 includes a detector 52, a pattern adjusting unit 53, the storage unit 40, the voltage controller 34, and the boosting circuit 35. The detector 52 configures the detecting unit according to the present disclosure and includes a current detector 54 and a resonant frequency operation unit 55. The current detector 54 measures the current flowing through the piezoelectric element 22. The resonant frequency operation unit 55 calculates the resonant frequency of the piezoelectric element 22 based on the current measured by the current detector 54. The pattern adjusting unit 53 grasps the sucked state of the breast by the breast pump cup 11 based on the resonant frequency calculated by the resonant frequency operation unit 55.

It should be noted that the pattern adjusting unit 53, the voltage controller 34, and the resonant frequency operation unit 55 can be configured by a microcomputer, for example. For example, when a microcomputer performing PWM control is used, an I/O terminal of the microcomputer is connected to the current detector 54 and a PWM output terminal of the microcomputer is directly connected to the boosting circuit 35. Furthermore, the microcomputer changes a duty ratio of PWM control output so as to control the driving voltage that is output from the boosting circuit 35.

FIG. 11 is a flowchart illustrating an example of operations of the driving controller 51 when the resonant frequency of the piezoelectric element 22 is detected as described above.

First, the driving controller 51 applies driving voltage set to have initial amplitude to the piezoelectric element 22 (S11). With this application, the piezoelectric element 22 is driven and the breast pump 10 starts an operation of absorbing breast milk using the breast pump cup 11. Then, the driving controller 51 stops application of the driving voltage to the piezoelectric element 22 (S12). Subsequently, the driving controller 51 waits for the predetermined time t1 on the halfway of the falling of the suction pressure, which is illustrated in FIG. 6A as described above, (Yes at S13) and measures the resonant frequency of the piezoelectric element 22 (S13→S34). Although the detailed description of the flow is omitted, as described above, the resonant frequency operation unit 55 calculates the resonant frequency of the piezoelectric element 22 by changing the frequency of the driving voltage that is output from the boosting circuit 35 controlled by the voltage controller 34 in the predetermined range, measuring the current flowing through the piezoelectric element 22 at each frequency, and selecting the frequency at which the amplitude of the measured current is maximum.

Then, the driving controller 51 compares the measured resonant frequency with a previously registered reference range (S35 and S37). When the measured resonant frequency is within the reference range (Yes at S35), the driving controller 51 keeps the driving voltage to the initial voltage and keeps the resting time to the predetermined setting (S16). When the measured resonant frequency is larger than the reference range (Yes at S37), the driving controller 51 changes the driving voltage to driving voltage having amplitude increased from that of the initial voltage and shortens the resting time from the predetermined setting (S18). When the measured resonant frequency is smaller than the reference range (No at S37), the driving controller 51 changes the driving voltage to driving voltage having amplitude decreased from that of the initial voltage and extends the resting time from the predetermined setting (S19).

Subsequently, the driving controller 51 sets the pattern of the driving voltage with the voltage amplitude and the length of the resting time that are set as described above and applies the driving voltage to the piezoelectric element 22 (S20). Then, the driving controller 51 repeats the application of the driving voltage to the piezoelectric element 22 (S20) and the stoppage of application of the driving voltage (S21).

As described above, when the pattern of the driving voltage to the piezoelectric element 22 is controlled by detecting the resonant frequency of the piezoelectric element 22, vibration of piezoelectric element 22 can be increased without changing the amplitude of the driving voltage by adjusting the frequency of the driving voltage to the resonant frequency measured by the detector 52. With this, high suction pressure can be provided even with the power consumption same as those in other embodiments or power consumption can be further reduced even with the suction pressure same as those in other embodiments.

With the driving controller 51 described herein, the resonant frequency is larger than the reference range when the skin of the breast surface is harder than the reference whereas the resonant frequency is smaller than the reference range when the skin of the breast surface is softer than the reference. However, depending on the configuration of the suction pump 21 and the configuration of the driving controller 51, conversely, the resonant frequency is smaller than the reference range when the skin of the breast surface is harder than the reference whereas the resonant frequency is larger than the reference range when the skin of the breast surface is softer than the reference in some cases. Therefore, it is preferable that the amplitude of the driving voltage and the resting time in the above-described operation flow be appropriately set based on the actual correspondence relation between the hardness of the skin of the breast surface and the resonant frequency.

10 BREAST PUMP
11 BREAST PUMP CUP
13 SEPARATOR
14 STORAGE CONTAINER
15 PIEZOELECTRIC DRIVING UNIT
16 FLOW PATH
21 SUCTION PUMP
22 PIEZOELECTRIC ELEMENT
23 STRUCTURAL BODY
24 FLOW PATH
25 PUMP CHAMBER
26 DISCHARGE PORT
27 SUCTION PORT
28 DIAPHRAGM
31, 41, 51 DRIVING CONTROLLER 32, 42, 52 DETECTOR
33, 43, 53 PATTERN ADJUSTING UNIT
34 VOLTAGE CONTROLLER
35 BOOSTING CIRCUIT
39 INDICATOR
44, 54 CURRENT DETECTOR
45 VOLTAGE DETECTOR
46 PHASE COMPARATOR
47 RESISTOR
55 RESONANT FREQUENCY OPERATION UNIT

The invention claimed is:

1. A breast pump comprising:
a suction unit adapted to be mounted on a breast;
a suction pump absorbing a fluid from a breast side of the suction unit that is adapted to contact the breast;
a detecting unit detecting a temporal change in a sucked state of the breast by the suction unit; and
a controller performing a processing based on the temporal change in the sucked state detected by the detecting unit,
wherein the detecting unit detects the sucked state of the breast by the suction unit based on a suction pressure of the suction pump,
wherein the suction pump includes a piezoelectric element operated by an application of a driving voltage, and
wherein the detecting unit detects an impedance state of the piezoelectric element and detects the suction pressure of the suction pump based on the detected impedance state of the piezoelectric element.

2. The breast pump according to claim 1, further comprising a storage unit previously storing a correspondence relation between the impedance state of the piezoelectric element and the suction pressure of the suction pump, wherein the detecting unit detects the suction pressure of the suction pump by referring to the storage unit.

3. The breast pump according to claim 2, wherein the detecting unit detects an amplitude of an electric current flowing through the piezoelectric element as the impedance state of the piezoelectric element.

4. The breast pump according to claim 3, further comprising a notification unit making a notification of the sucked state detected by the detecting unit.

5. The breast pump according to claim 2, wherein the detecting unit detects a phase difference between the electric current flowing through the piezoelectric element and a driving voltage of the piezoelectric element as the impedance state of the piezoelectric element.

6. The breast pump according to claim 5, further comprising a notification unit making a notification of the sucked state detected by the detecting unit.

7. The breast pump according to claim 2, wherein the detecting unit detects a resonant frequency of the piezoelectric element as the impedance state of the piezoelectric element, and the controller drives the piezoelectric element at the resonant frequency.

8. The breast pump according to claim 7, further comprising a notification unit making a notification of the sucked state detected by the detecting unit.

9. The breast pump according to claim 2, further comprising a notification unit making a notification of the sucked state detected by the detecting unit.

10. The breast pump according to claim 1, further comprising a notification unit making a notification of the sucked state detected by the detecting unit.

* * * * *